United States Patent
Schachameyer et al.

(10) Patent No.: US 6,844,745 B1
(45) Date of Patent: Jan. 18, 2005

(54) METHOD OF DETERMINING THE FLUID CONDITION OF DIESEL ENGINE LUBRICANT DURING REAL TIME OPERATION

(75) Inventors: Steven R. Schachameyer, deceased, late of Mequon, WI (US); by Sher Schachameyer, legal representative, Mequon, WI (US); Richard W. Hirthe, Milwaukee, WI (US); Anne M. Brunson, Grafton, WI (US); Victor E. Shtaida, Franklin, WI (US); Lian Q. Zou, Glendale, WI (US); Charles J. Koehler, Milwaukee, WI (US)

(73) Assignee: Eaton Corporation, Cleveland, OH (US)

( * ) Notice: Subject to any disclaimer, the term of this patent is extended or adjusted under 35 U.S.C. 154(b) by 0 days.

(21) Appl. No.: 10/662,588

(22) Filed: Sep. 15, 2003

(51) Int. Cl.[7] .................................................. G01R 27/08
(52) U.S. Cl. .................................... 324/698; 324/691
(58) Field of Search ................................ 73/53.05, 116; 324/439, 691, 698; 340/631; 508/110

(56) References Cited

U.S. PATENT DOCUMENTS

| | | | |
|---|---|---|---|
| 5,604,441 A | * | 2/1997 | Freese et al. ............... 324/663 |
| 6,278,281 B1 | | 8/2001 | Bauer et al. ................ 324/441 |
| 6,377,052 B1 | | 4/2002 | McGinnis et al. .......... 324/446 |
| 6,380,746 B1 | | 4/2002 | Polczynski et al. ......... 324/446 |
| 6,433,560 B1 | | 8/2002 | Hansen et al. .............. 324/668 |
| 6,509,745 B1 | * | 1/2003 | Marszalek ................... 324/663 |
| 6,590,402 B2 | * | 7/2003 | Wang et al. ................. 324/698 |
| 2004/0036487 A1 | * | 2/2004 | Heremans et al. .......... 324/698 |

* cited by examiner

Primary Examiner—N. Le
Assistant Examiner—Walter Benson
(74) Attorney, Agent, or Firm—Roger A. Johnston

(57) ABSTRACT

A probe having a pair of electrodes is excited with a low A.C. voltage at a relatively high and relatively low frequency and the difference in current measured. The difference dZ between bulk fluid and interfacial impedance is computed from the current difference. The rate of change $\Delta dZ$ of the impedance difference is determined over a time interval and a physiochemical parameter (X) determined when $\Delta dZ$ is positive from lubricant with known amounts of constituents selected from the group consisting of (a) Phosphorus, Oxygen and Carbon (P—O—C); (b) Phosphorous and double bond Sulphur (P=S); (c) Zincdialkyldithiophosphate (ZDDP); and (d) the Total Base Number TBN by measuring $CaCO_3$ (CO3), from a table of the selected parameter X versus dZ in a first region of the table and determining RUL from a table of RUL versus parameter X ($X_1$). The value of the selected parameter X when $\Delta dz$ is negative is determined from a second region of the table of X versus dZ. The rate of change $\Psi$ of X over a time interval is determined and RUL determined from a known value of $X_{EOL}$ for the end of the lubricant life.

4 Claims, 10 Drawing Sheets

METHOD OF DETERMINING THE FLUID CONDITION OF DIESEL ENGINE LUBRICANT DURING REAL TIME OPERATION

BACKGROUND OF THE INVENTION

The present invention relates to monitoring the condition of a fluid such as Diesel engine lubricant while the engine is running and providing an electrical signal indicative of the condition of the fluid insofar as its ability to continue its function to effectively lubricate the running engine.

A known technique for monitoring engine lubricant during real time operation is that employing impedance spectroscopy wherein a pair of electrodes are immersed in the lubricant sump and one electrode excited with a low level alternating current voltage at a relatively high and then sequentially at a relatively low frequency and from the current measurements at both frequencies the impedance is computed and the differential impedance correlated with known properties of the fluid at various stages of lubricant stressing. The differential impedance may then be compared with the known values in real time to determine from a lookup table of the differential impedance versus known fluid conditions what the instantaneous condition of the fluid is during engine operation.

Such a lubricant monitor employing impedance spectroscopy techniques is shown and described in U.S. Pat. Nos. 6,278,281, 6,377,052, 6,380,746 and 6,433,560 which are assigned to the assignee of the present invention. The aforesaid '281 patent particularly describes a technique for utilizing impedance spectroscopy to determine the presence of engine coolant in automatic transmission fluid and in passenger car motor oil.

U.S. Pat. No. 6,377,052 describes a method of monitoring synthetic motor oil of the type employed in spark ignition gasoline fueled engines in passenger cars utilizing impedance spectroscopy for determining during real time operation the instantaneous remaining useful life (RUL) of the engine lubricant by comparison of impedance calculated from sequential current measurements at different frequencies for engine oil of a known condition.

However, it has been desired to also monitor, during real time engine operation the condition of lubricant in compression ignition or Diesel engines. In Diesel engines, the lubricant is blended by the lubricant manufacturer with unique additive systems or constituents to prevent deterioration of the lubricant due to the effects of the products of combustion of Diesel fuel. Thus Diesel engine lubricant is formulated with additives having a substantially different chemical composition from that of lubricant formulated for spark ignition engines burning gasoline or other fuels. Accordingly, it has been desired to find techniques and ways of employing impedance spectroscopy to accurately provide an electrical indication, during real time engine operation, of the condition of the lubricant in Diesel engines.

BRIEF SUMMARY OF THE INVENTION

The present invention employs a probe having a pair of electrodes immersed in the engine lubricant and applies impedance spectroscopy techniques by exciting one probe with a low amplitude alternating current voltage sequentially at relatively high and low frequencies and measuring the current at both frequencies and using the difference in the current as an analog of the impedance change. The impedance difference is compared with values measured for samples of Diesel lubricant having known characteristics of additive depletion from a lookup table and from this a percentage RUL determined.

The method of the present invention utilizes the propensity of the impedance difference (dZ) to increase to a maximum when the fluid is new or partially stressed and the propensity of dZ to decrease from a maximum occurring during moderate stress to its lowest value when the fluid is fully stressed and has reached near zero RUL. The method determines the rate of change or slope of the impedance difference ($\Delta dZ$) during a selected sampling interval; and, where $\Delta dZ$ is positive, the readings are correlated with a first Region of the lookup table of known values of additive depletion; and, where $\Delta dZ$ is negative from a second Region of the lookup table. In the present practice of the invention, the tables are compiled by measuring the values of depletion of a parameter X selected from a group consisting of (a) Phosphorus, Oxygen, Carbon (P—O—C), (b) Phosphorus and double bond Sulphur (P=S), (c) acidity or total base number (TBN) as a function of Calcium Carbonate Depletion ($CO_3$) or (d) depletion of Zincdialkyldithiophosphate (ZDDP). The tables of known values of fluid condition or RUL are determined individually for each of the parameters (a)–(d) above from laboratory measurements by Fourier Transform Infrared Spectroscopy (FTIR) techniques of lubricant samples taken from Diesel engines at known condition levels of lubricant stressing.

DETAILED DESCRIPTION OF THE INVENTION

Figure 1:
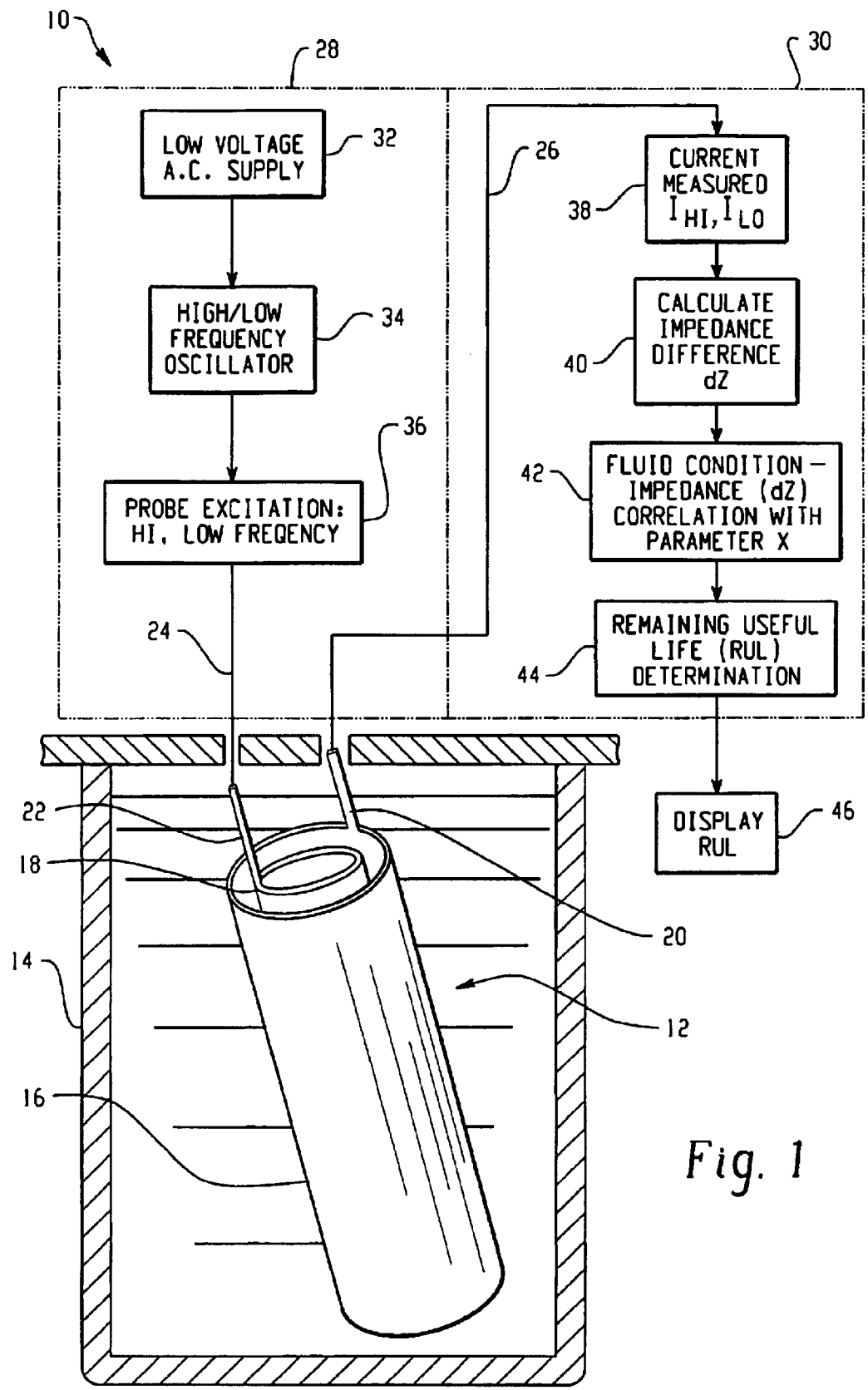
FIG. 1 is a pictorial and block diagram of the system employing the method of the present invention.

Referring to FIG. 1, the system of the present invention is indicated generally at 10 which includes a probe indicated generally at 12 having a tubular configuration and comprising an outer pickup or measurement electrode 16 radially spaced from and concentrically surrounding an inner tubular electrode 18, each of which has respectively a connector strip 20, 22 extending axially therefrom for electrical connection thereto. An electronic controller 10 has a lead 24 therefrom connected to terminal strip 22 and a lead 26 connected to the terminal strip 20. In the presently preferred practice of the invention, the probe is configured as shown and described in co-pending application Ser. No. 10/060,107 Filed Jan. 31, 2002, entitled "Probe Assembly For A Fluid Condition Monitor And Method Of Making Same" published Aug. 5, 2003 as U.S. Patent Publication 2003-0141,882 and assigned to the assignee of the present invention. However, other probe configurations may be employed such as planar interdigitated electrodes, or helically configured electrodes as described in the aforesaid U.S. Pat. Nos. 6,278,281, 6,380,746 and 6,377,052.

Controller 10 includes a signal generating or excitation section 28 and a signal processing and output section 30.

The excitation section 28 functions to provide a relatively low amplitude alternating current voltage of not more than about one Volt. In the present practice of the invention, the probe was excited with 0.750 Volts RMS; however, other voltage levels may be used in order to provide a useable signal-to-noise ratio. Section 28 includes the power supply 32 and includes an oscillator 34 which provides a relatively high and low frequency current to a probe excitation circuit 36 which sequentially excites electrode 18 along line 24 at the high and low frequencies. In the present practice of the invention the low frequency is chosen at about 30 milliHertz and the high frequency at about 100 Hertz. It will be understood that the low frequency may be varied so long as it is indicative of the electrode surface characteristics and the high frequency varied so long as it is indicative of bulk fluid properties. The low frequency is preferably in the range 10–100 milliHertz and the high frequency preferably in the range 10–10,000 Hertz.

The signal processing section receives the probe current along line 26 to the current sensing circuit 38 which provides inputs to computer 40 which calculates the impedance difference dZ. Computer 40 provides an input to comparison circuitry 42 which is operative to correlate the impedance difference dZ with known values of a fluid condition parameter X, as will hereinafter be described, which provides an input to computer 44 which determines RUL and provides an output to the display 46.

Figure 2A:
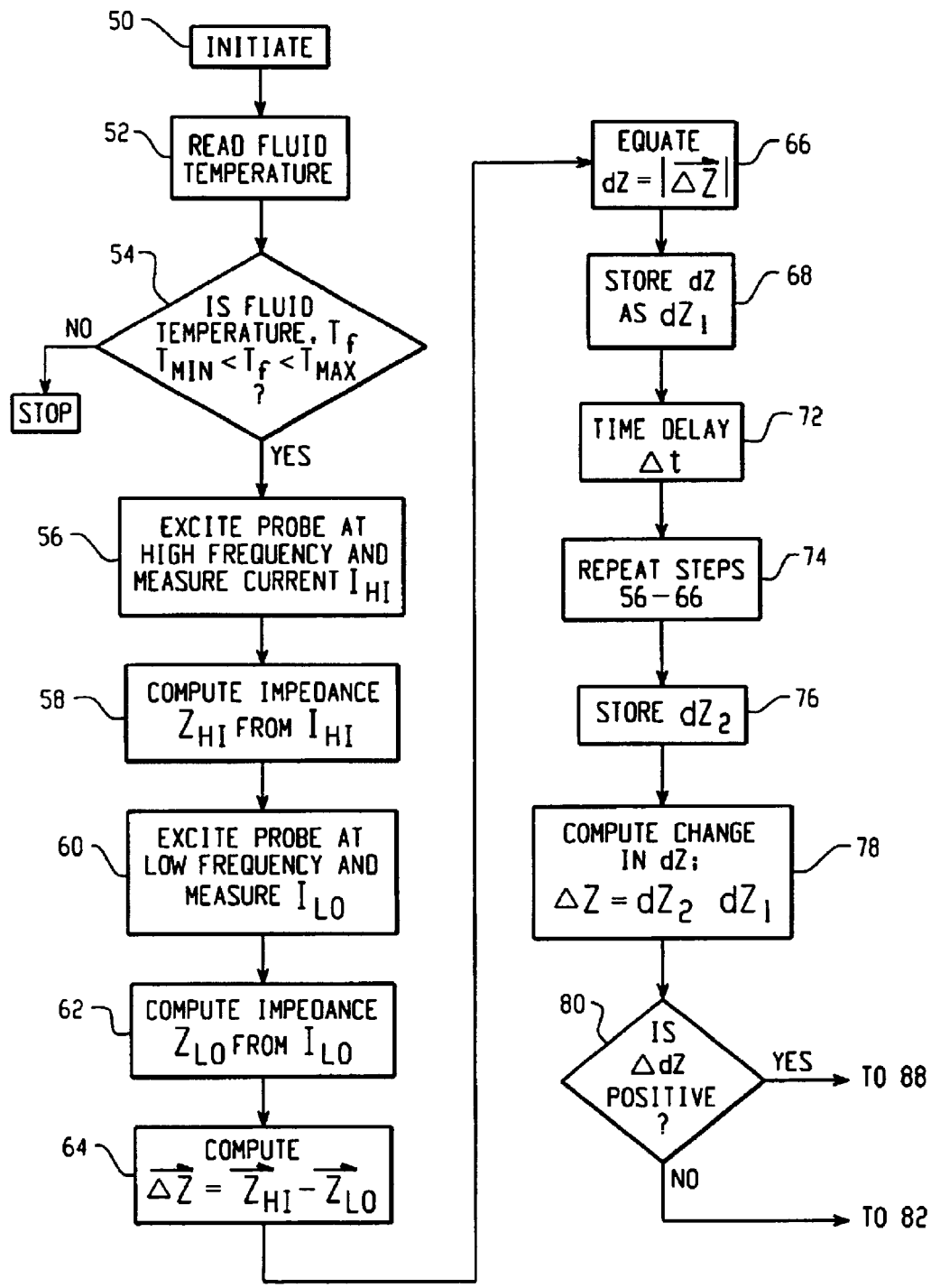
FIGS. 2a, 2b and 2c comprise a block diagram of the signal processing strategy of the method of the present invention.
Figure 2B:
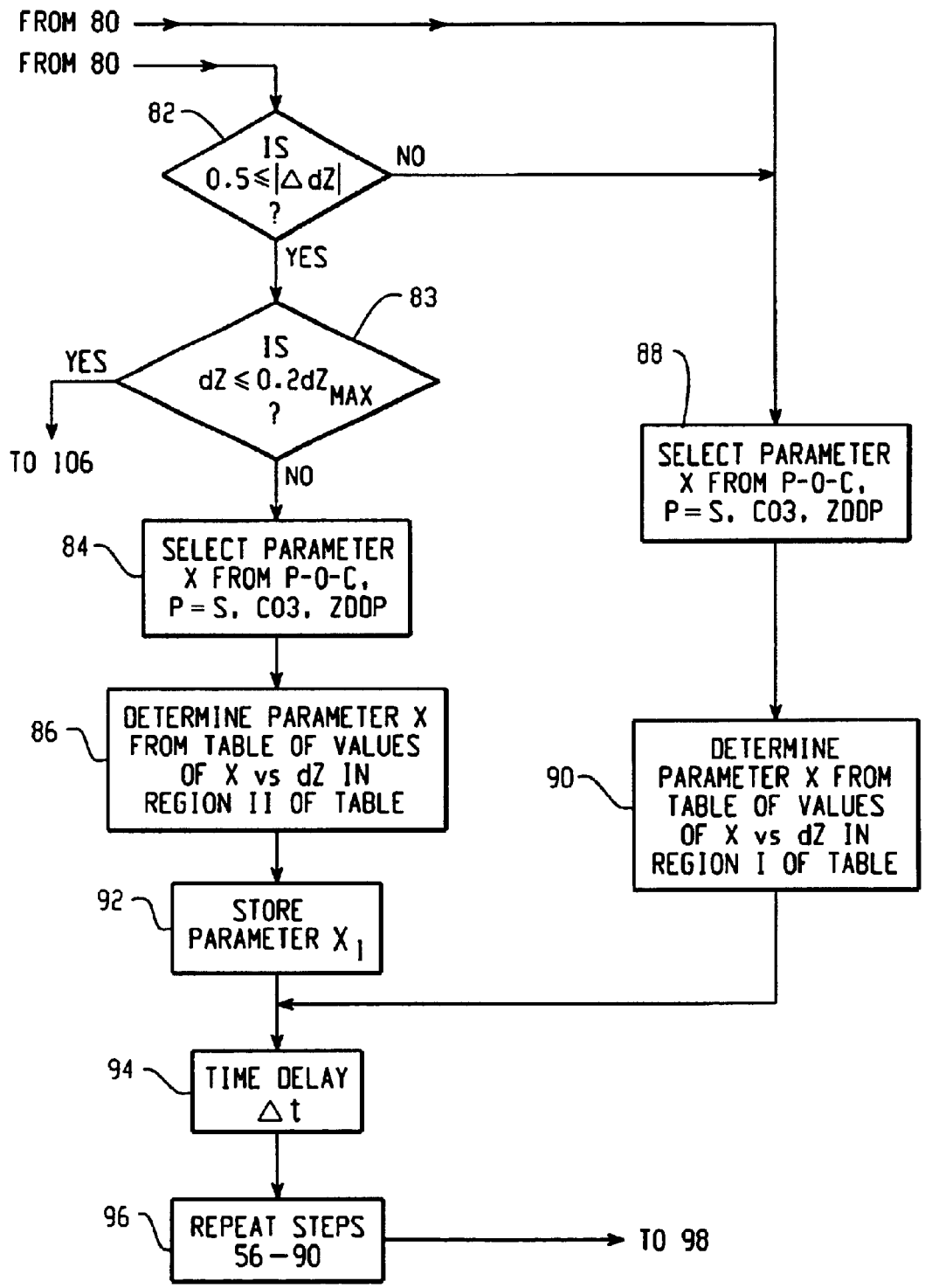
Figure 2C:
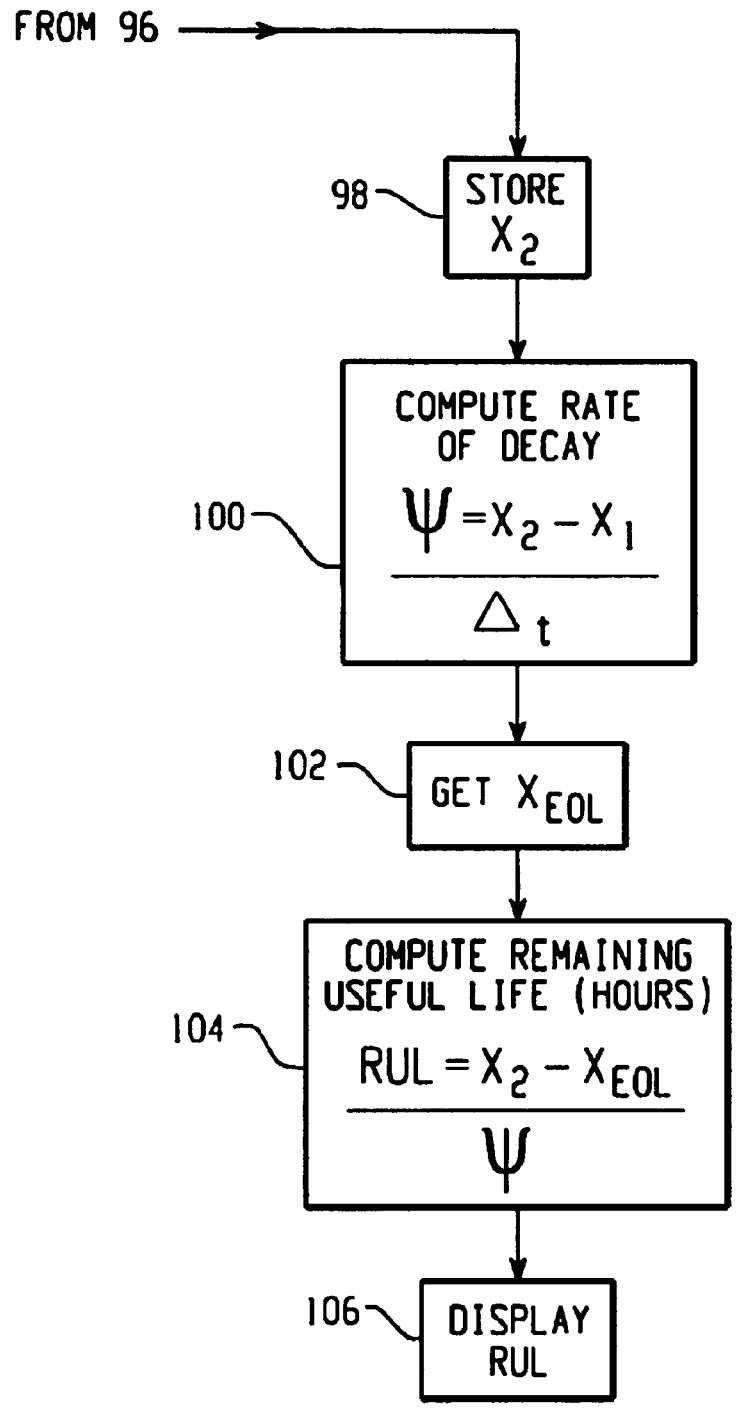
Figure 3:
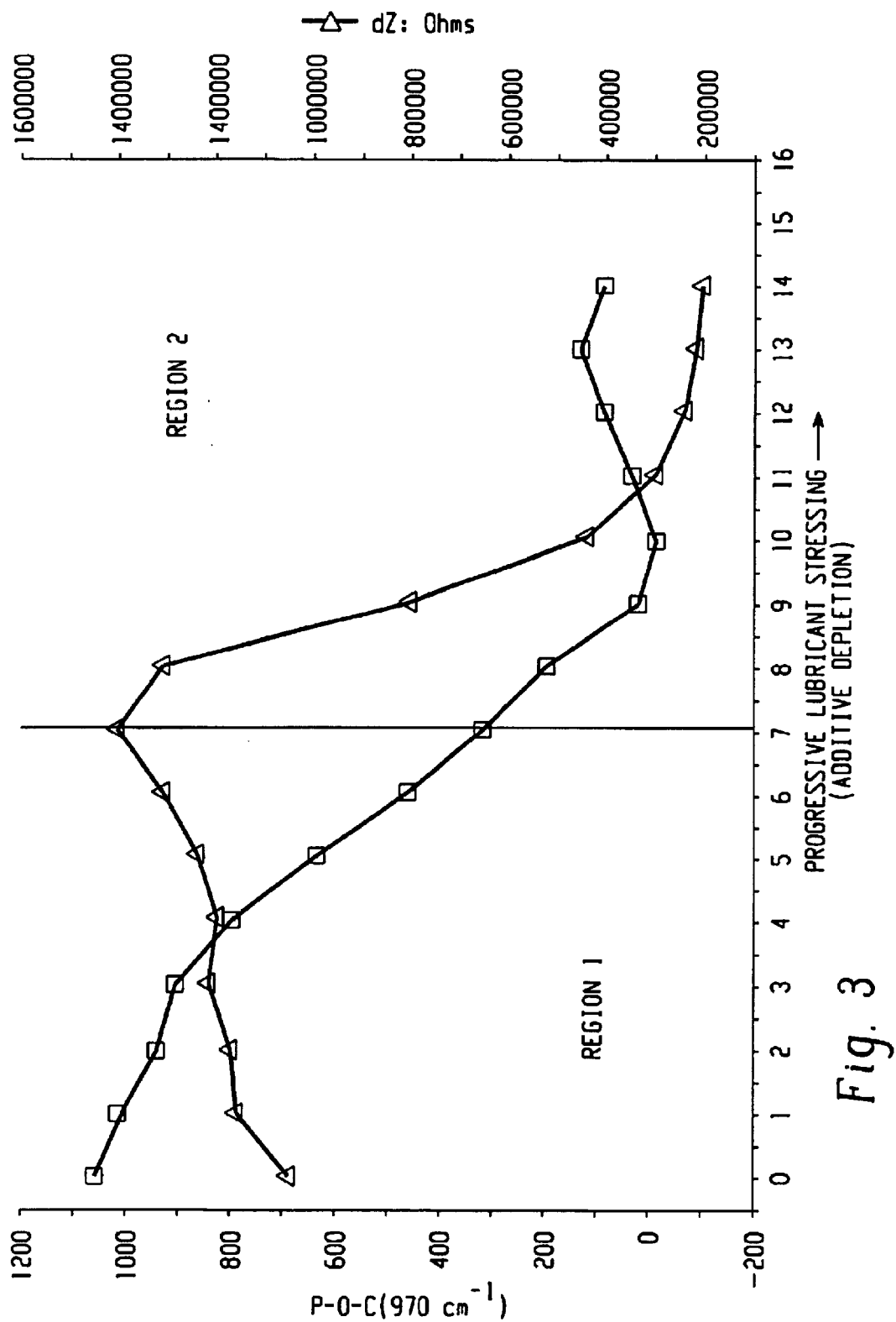
FIG. 3 is a graph plotting values of POC and dZ for lubricant samples having progressively increased stressed condition.
Figure 4:
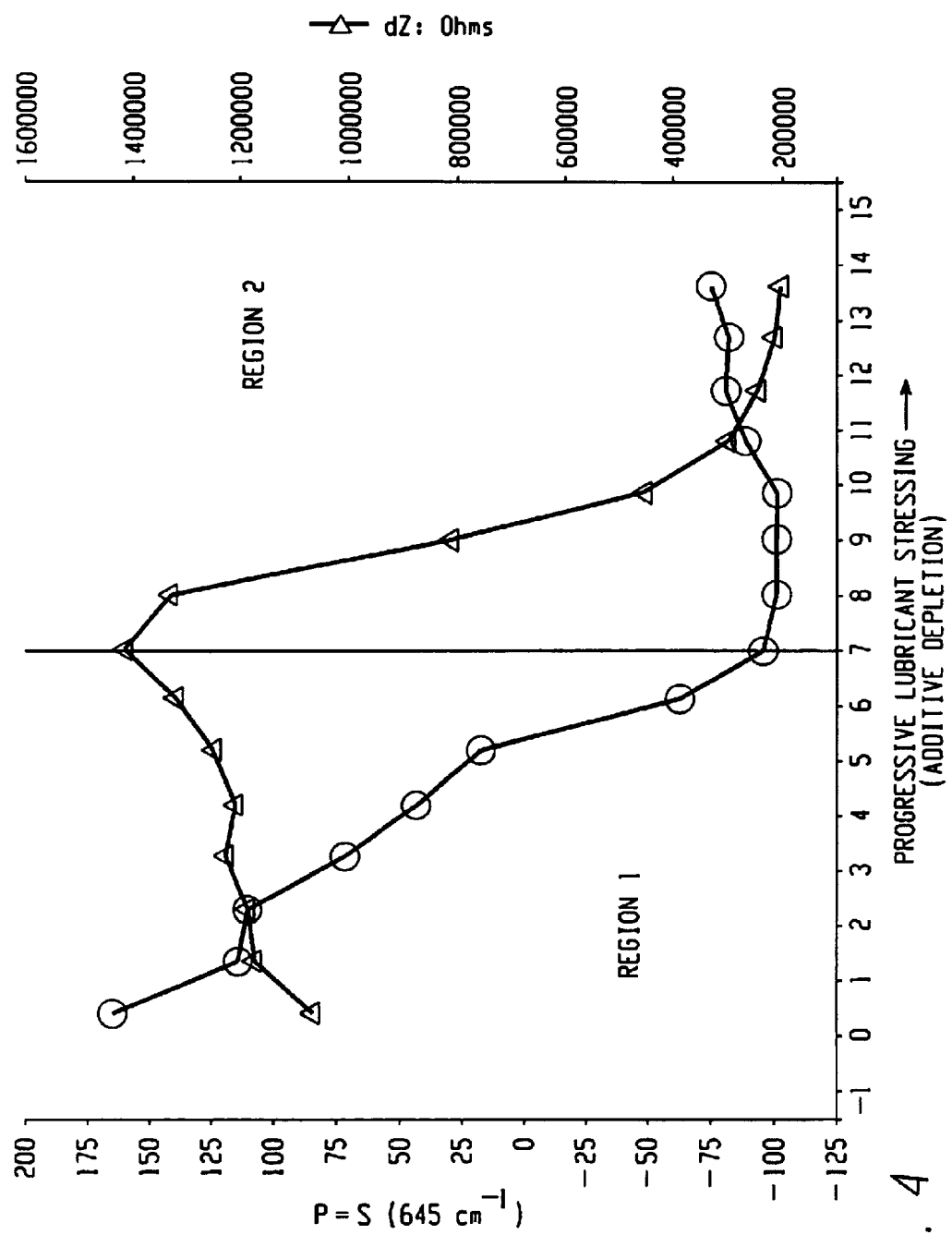
FIG. 4 is a graph similar to FIG. 3 for P=S as a function of lubricant stressing.
Figure 5:
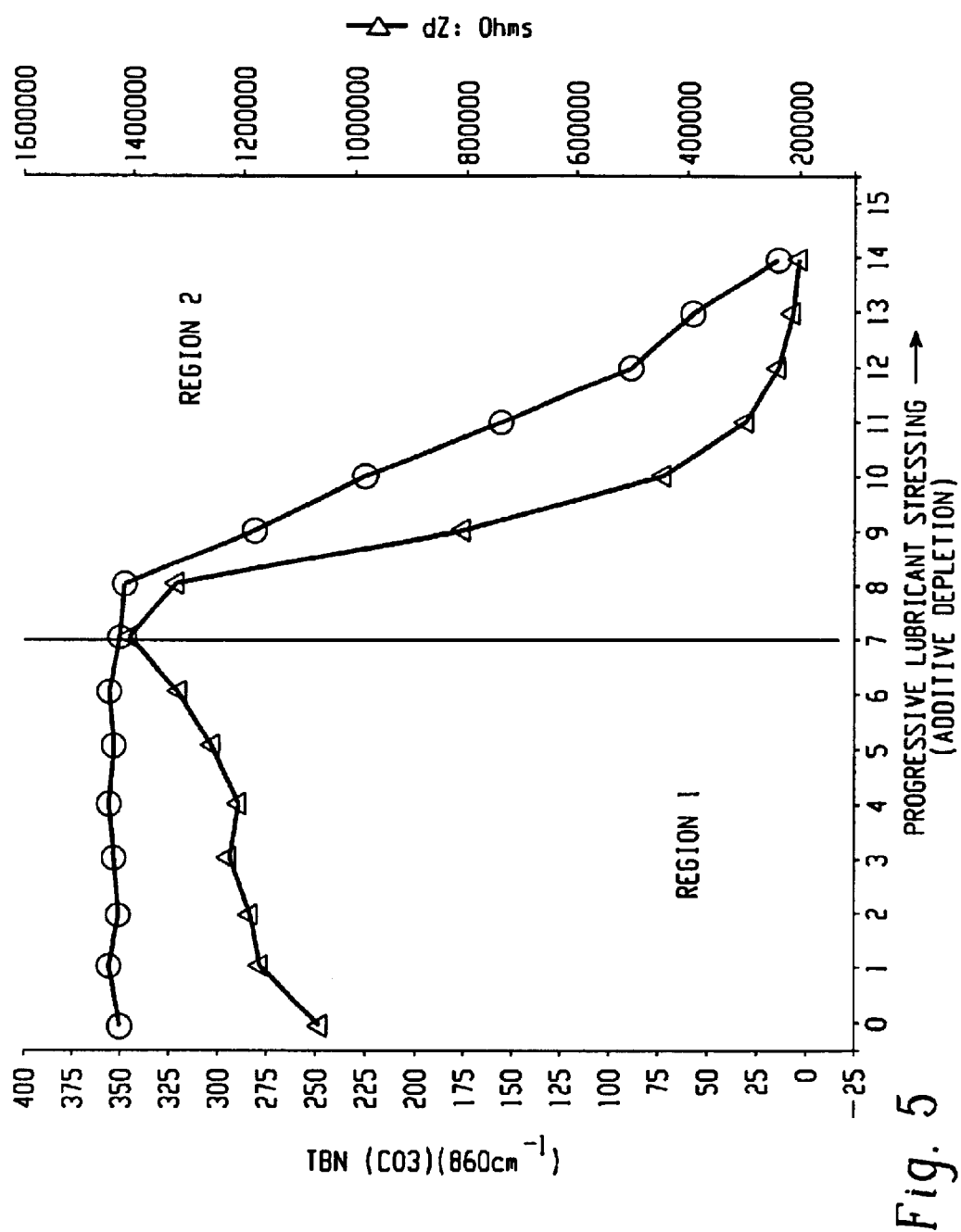
FIG. 5 is a graph similar to FIG. 3 for TBN or carbonate depletion for progressively stressed lubricant.
Figure 6:
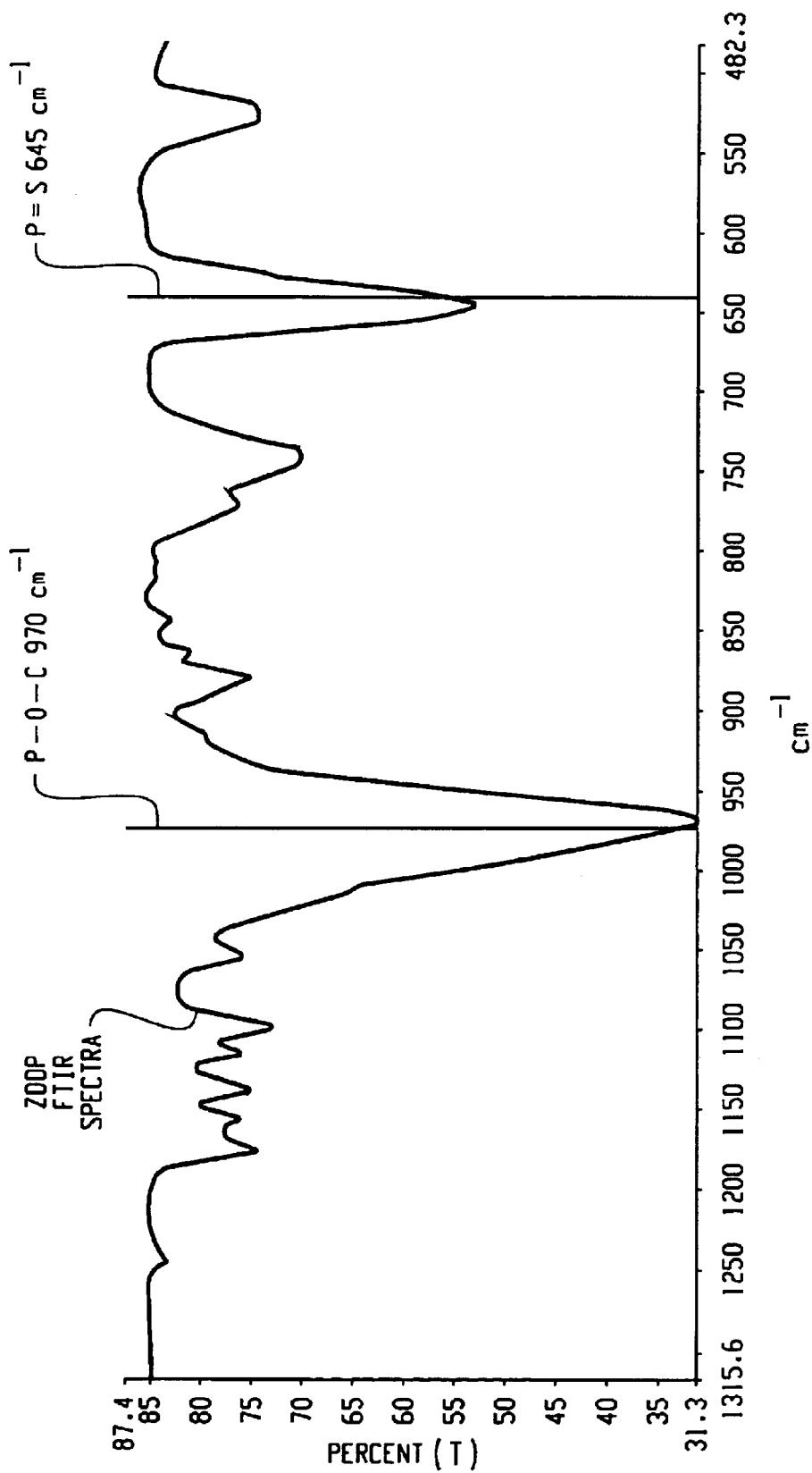
FIG. 6 is an FTIR transmittance spectra trace of ZDDP as formulated prior to being added to the lubricant.

Referring to FIG. 2, the signal processing strategy of the signal generating section 28 and signal processing section 30 of the electronic controller 10 is illustrated wherein upon initiation at step 50, the computer 40 receives a fluid temperature input at step 52 from a temperature sensor (not shown) and proceeds to step 54 to ask whether the temperature of the fluid $T_f$ is within minimum and maximum permissible limits $T_{MIN}$, $T_{MAX}$. If the determination of step 54 is negative, the system proceeds to hold or stop until the temperature is within the desired limits. When the determination at step 54 is affirmative, the system proceeds to step 56 and the excitation circuitry 36 excites the probe at the high frequency and the current sensor 38 measures the current $I_{HI}$. The system then computes the impedance $Z_{HI}$ at step 58 and proceeds to step 60 where the circuitry 36 excites the probe at the low frequency and sensor 38 measures the current $I_{LO}$. The system then proceeds to step 62 and computes the impedance $Z_{LO}$ from the current measurement $I_{LO}$. The system then proceeds to step 64 and computes the impedance difference $\Delta Z$ and proceeds to step 66 and takes the absolute value of $\Delta Z$ as impedance difference dZ.

The system then proceeds to step 70 and stores dZ as $dZ_1$ and then proceeds to step 72 for a predetermined time delay and then proceeds to step 74 and repeats steps 56 through 66 and proceeds to step 76 to store the results as $dZ_2$. In the present practice of the invention the time delay $\Delta t$ in step 72 has been found to be satisfactory if set at about two hours; however, any suitable period may be chosen which enables accurate determination of the change in dZ. The system through computer 44 then proceeds to step 78 and computes the change $\Delta dZ$ in dZ. The computer then proceeds to step 80 and asks whether $\Delta dZ$ is positive; and, if the computer proceeds to step 88 and selects the parameter X chosen from the group (a) Phosphorous, Oxygen, Carbon P—O—C, (b) Phosphorous double bonded with Sulphur P=S, (c) Calcium Carbonate, $CaCO_3$, CO3 and (d) Zincdialkyldithiophosphate ZDDP and then proceeds to step 90 to determine the parameter X from a table of values of X versus dZ in a region I of the table.

It will be understood that the table is compiled from data points taken from the graphs of FIGS. 3 through 6. The system then proceeds to step 92 for a predetermined time delay $\Delta t$.

If the determination at step 80 is negative the computer proceeds to step 82 and asks whether the absolute value of the slope is equal to or greater than about 0.5. If the determination at step 82 is negative, the system proceeds to step 88.

However, if the determination of step 82 is positive, meaning that the negative slope of $\Delta dZ$ is rather steep, the computer proceeds to step 83 and selects parameter X from one of the aforesaid parameters and then proceeds to step 84 to determine parameter X from a table of values of X versus dZ from a region II of a table compiled from one of FIGS. 3 through 6. The computer then stores the value determined as $X_1$.

The computer then proceeds to step 94 for a predetermined time delay $\Delta t$ and then proceeds to step 96 and repeats steps 56 through 90 and stores the result as $X_2$ at step 98.

The computer then proceeds to step 100 and computes the rate of decay $\Psi$ from the difference of $X_2$ and $X_1$ divided by $\Delta t$. The computer then retrieves a stored value of $X_{EOL}$ or the value of the parameter X at the end of the useful life for the lubricant and proceeds to step 104 to compute the remaining useful life (RUL) by subtracting XEOL from $X_2$ and dividing by the rate of decay $\Psi$.

The computer then outputs a signal to a display at step 106. It will be understood that the display may either be a running indicator or an alarm if a threshold level of RUL has been reached.

In the present practice of the invention, when the value of dZ has increased to a level of about twenty percent (20%) of its maximum peak value, the value determining the separation between region one and region two of FIGS. 3–6, the computer may be programmed to proceed directly to indicate an RUL of nearly zero.

In the present practice of the invention the graphs of FIGS. 3–6 are each obtained by taking a sequence of drain samples of Diesel engine lubricant at progressively increased levels of fluid stress. The samples are then tested by known FTIR techniques for the amount of P—O—C, P=S, CO3 and ZDDP by observing the spectral density in the regions set forth in Table I.

TABLE I

| PARAM. X | Nominal IR Freq. $CM^{-1}$ | IR Freq. Range $CM^{-1}$ |
|---|---|---|
| P—O—C | 970 | 1020–912 |
| P=S | 655 | 685–645 |
| CO3 (TBN) | 860 | 1597–1326 |
| ZDDP | 655, 970 | — |

Figure 7:
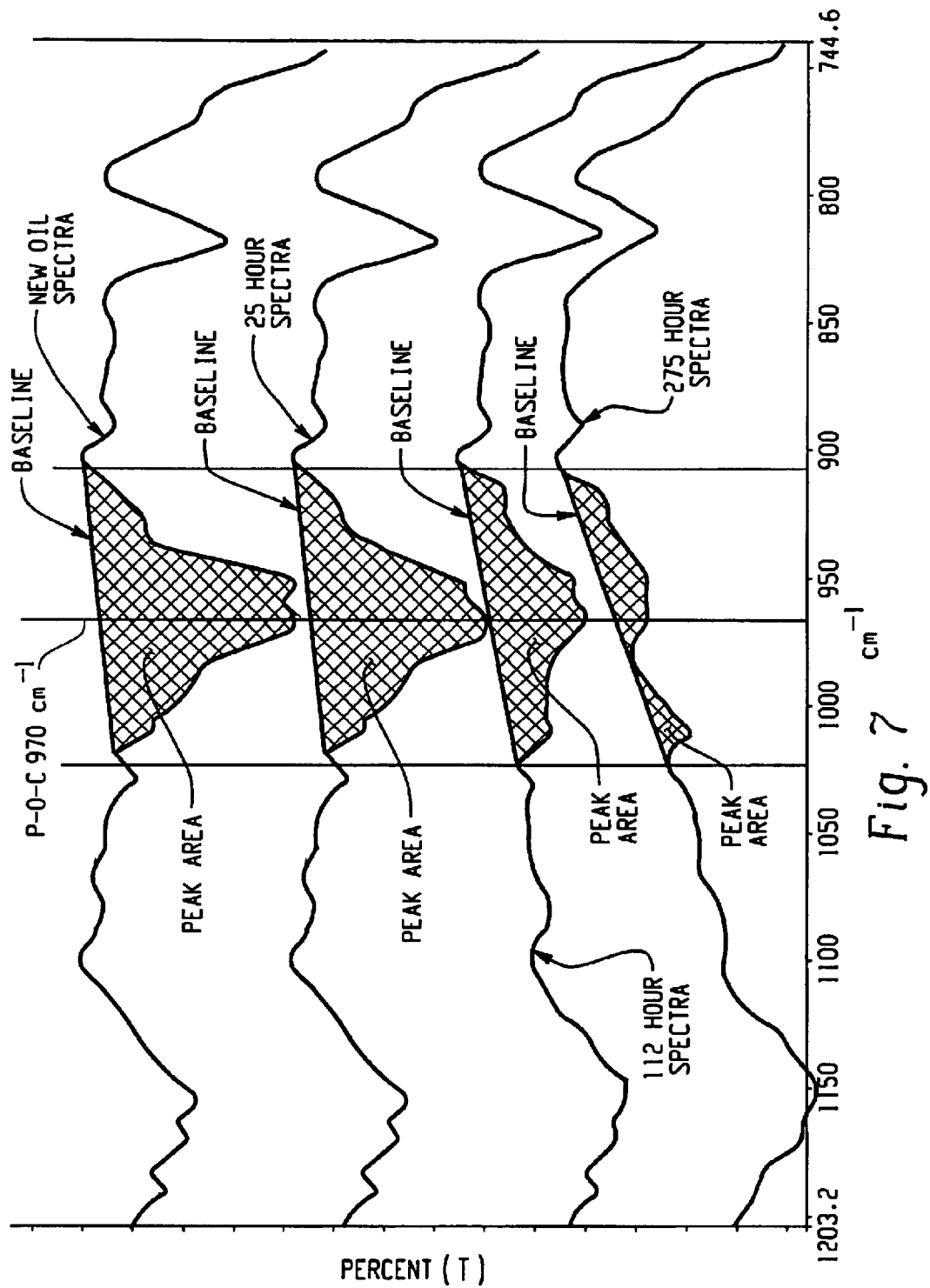
FIG. 7 is an FTIR transmittance spectra trace of lubricant samples taken from an engine at intervals of increased levels of stressing with the area below the baseline shaded in the frequency range of P—O—C; and, FIG. 8 is an FTIR of lubricant samples taken from an engine at intervals of increased levels of stressing with the area below the baseline shaded for the frequency range of P=S.

Referring to FIG. 7, a percentage transmission FTIR spectral trace is illustrated for ZDDP in an as-formulated condition prior to blending or addition to the engine lubricant. It will be noted from FIG. 7 that ZDDP undergoes an infrared transmission null at frequencies of 970 cm$^{-1}$ and 645 cm$^{-1}$ or, in other words, is completely absorbent at these frequencies. This characteristic of ZDDP has been found to be quite useful in spectroscopy inasmuch as the infrared transmission loss of the lubricant at these frequencies may be treated as an analog or indication of the percentage of the ZDDP remaining or undepleted in the particular sample of lubricant.

Figure 8:
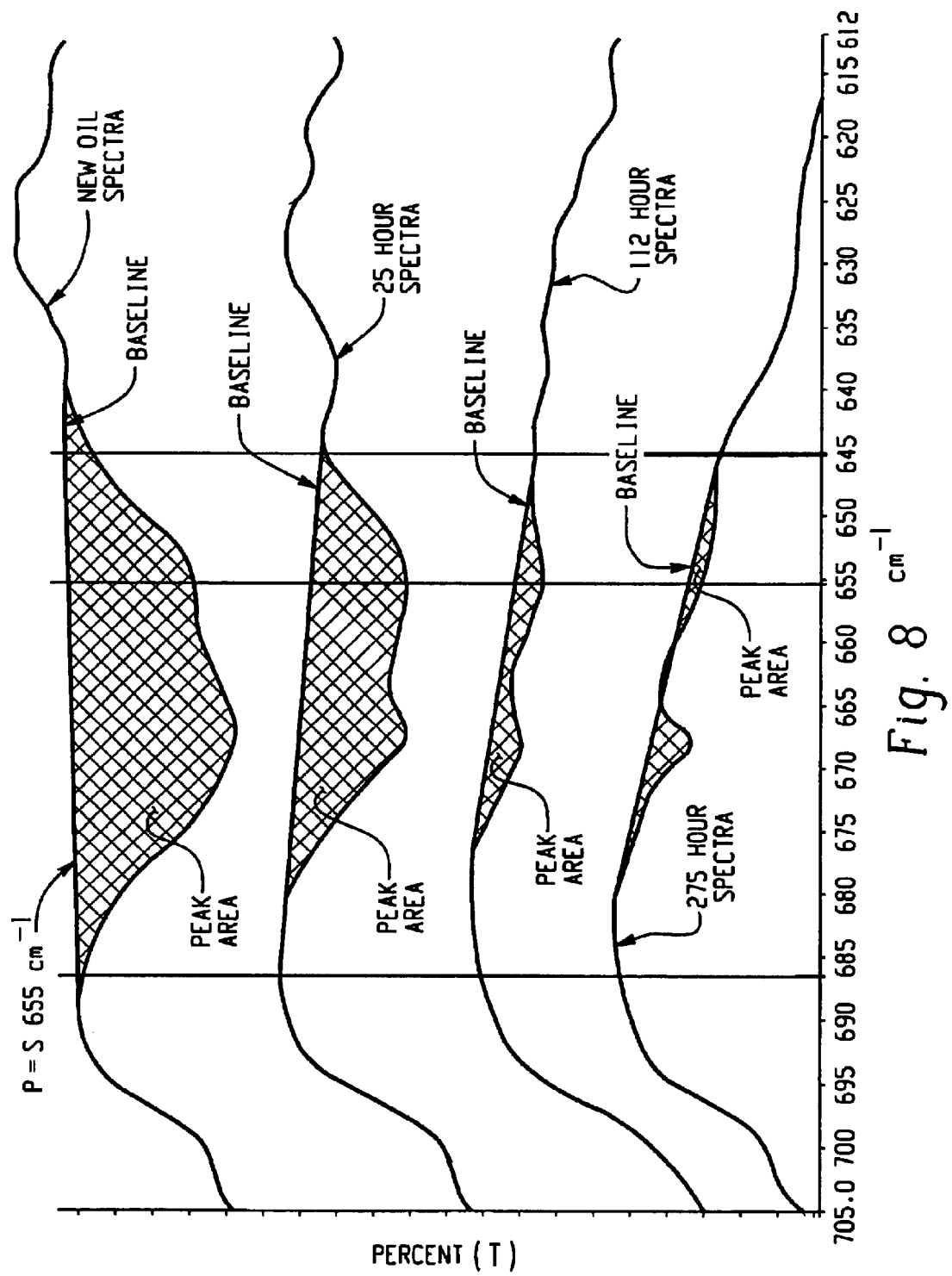

Referring to FIGS. 7 and 8, samples of engine oil drained at selected intervals of 25 hours, 112 hours and 275 hours engine operation have been taken; and, the spectral traces plotted for each of the samples along with a trace of new oil for the frequency bands of interest surrounding the 970 cm$^{-1}$, 655 cm$^{-1}$ nominal frequencies which correspond to the frequencies for P—O—C and P=S respectively. The technique employed utilizes a baseline drawn between the peaks for each sample trace occurring within the frequency band of interest as set forth in Table I. The area formed by the trace under the baseline in the frequency band examined, shown as shaded in FIGS. 7 and 8, is computed and the decrease in the area measured for each sample of known stress level condition. The percentage depletion of ZDDP is then known and the sample may be measured with the probe of the present invention and the change in impedance dZ measured and a table of values of percentage depletion as a function of dZ established. Thus, it will be seen from FIGS. 7 and 8 that if a sample of stress lubricant is analyzed by the aforesaid FTIR technique and the result indicates nearly zero area of the trace under the baseline in the region of observance, there will be nearly no absorbance at the frequency under examination and thus the ZDDP will have been totally depleted.

Referring again to FIGS. 3 and 4, it will be seen that from the plots of P=S and P—O—C as a function of increased lubricant stressing that a value of the sensor output dZ may be chosen which corresponds to the minimum value of P—O—C in region to representing total depletion of ZDDP; and, this value of dZ may be chosen as the end of life for the lubricant. Similarly, in FIG. 4 the plot of P=S as a function of progressive lubricant stressing indicates that the minimum is reached corresponding to total additive depletion at about the same value of dZ as that indicated in FIG. 3 for P—O—C. Thus, a lookup table of values of dZ as a function of the lubricant condition may be compiled utilizing the spectra at the selected frequencies as an indication of the amount of ZDDP remaining in the lubricant.

Weak acidity TBN (CO3) may also be measured by American Society For Testing Materials (ASTM) standard D4739-2 "Standard Test Method For Base Number Determination By Potentiometric Titration".

The graphs in FIGS. 3 through 6 are based upon data taken from samples of Diesel engine oil sequentially as the lubricant is progressively stressed as measured by the present technique; and, the value of dZ is computed for the sample according to steps 50–70. The amount of each of the lubricant blend additives listed in Table I is then determined separately by FTIR laboratory analysis. A table of correlated values of dZ for each additive type is then compiled and the data sets may be plotted as has been done in FIGS. 3–6. The scale on the horizontal or "X" axis in FIGS. 3 through 6 thus represents sequential samples taken at selected intervals in the progressive stressing of the lubricant. It will be understood the zero on the horizontal axis in FIGS. 3 through 6 represents new oil; and, 14 on the horizontal axis represents an oil sample of the same oil, at the end of its useful life as determined by the aforesaid laboratory analysis, that is when all additives are chemically depleted. It will be observed from the plots of FIGS. 3 through 6 that dZ increases in Region I where the lubricant has only been moderately stressed to a maximum value and then dZ decreases thereafter as the lubricant is further stressed to the end of the useful life (EOL) of the lubricant.

One of the additives from the group may then be selected and the data from the table or graph programmed into the computer 40,42 in section 30 of the circuitry 10, thereby enabling real time correlation of dZ with RUL for the lubricant. The data for FIGS. 3–6 of the present invention was determined from American Petroleum Institute (API) category CH4, CF oil with SAE 25-W40 viscosity rating. It will be understood however that the technique of the present invention may be employed with Diesel lubricants of other API categories (such as CF-4, CG-4 and CF-2 by way of example without limitation and other SAE viscosity ratings such as SAE 30 and SAE 25 W-40 by way of example without limitation.

It will be understood that computer circuitry 42 may be programmed with a lookup table taken from any one of FIGS. 3–6 depending upon which chemical type of blend additive it is desired to track with the monitor. Furthermore, it will be understood that the value of dZ assigned to represent nearly zero RUL may be varied in accordance with engine manufacturers recommendation as to additive depletion; and, thus the threshold of determination at step 83 may be chosen other than 0.2 (20%) of $dZ_{MAX}$ as desired or upon the engine manufacturer's recommendation.

The present invention thus provides a convenient method of employing impedance spectroscopy to provide an indication of the instantaneous condition of lubricant during real time operation of a Diesel engine. The present invention utilizes a probe having spaced electrodes immersed in the lubricant sump with an electronic controller attached to the electrodes such that current measurements, upon low level AC voltage excitation measured sequentially at a relatively high and low frequency, enable an impedance differential to be computed and compared with stored values determined for Diesel lubricant of known condition. The electronic controller may then, from the comparison, determine and provide an indication of the remaining useful life of the lubricant or an alarm indication to the engine operator.

Although the invention has hereinabove been described with respect to the illustrated embodiments, it will be understood that the invention is capable of modification and variation and is limited only by the following claims.

What is claimed is:

1. A method of monitoring the conditions of engine lubricant in real time during operation comprising:

(A) immersing a probe with a pair of spaced parallel conductors in the fluid to be monitored;

(B) exciting of said pair of electrodes with an alternating voltage at a first relatively high frequency and exciting said one conductor at a second relatively low frequency and measuring the current at said first and second frequencies;

(C) computing the bulk fluid impedance at said first frequency and the fluid-electrode interface (surface) impedance at the said second frequency and computing the impedance difference (dZ) therefrom;

(D) delaying for a selected time interval and repeating steps (A)–(C) and computing another value of dZ;

(E) computing the rate of change of dZ ($\Delta dZ$) for a selected time interval ($\Delta t$) and determining the value of the remaining useful life (RUL) of the lubricant from the following:

(i) determining the value of a physiochemical parameter (X) when $\Delta dZ$ is positive from lubricant with known amounts of constituents selected from the group consisting of (a) Phosphorus, Oxygen and Carbon (P—O—C); (b) Phosphorous and double bond Sulphur (P=S); (c) Zincdialkyldithiophosphate (ZDDP); and (d) the Total Base Number TBN by measuring $CaCO_3$ (CO3), from a table of the selected parameter X versus dZ in a first region of the table and determining RUL from a table of RUL versus parameter X ($X_1$);

(ii) determining the value of the selected parameter X when $\Delta dZ$ is negative from a second region of the table of X versus dZ;

(F) repeating steps (B)–(E) after a selected time delay $\Delta t$ and determining a second value of X ($X_2$) computing the rate of change of X, $$\Psi = \frac{X_2 - X_1}{\Delta t};$$

and, (G) computing the remaining useful life (RUL) expressed as a percentage by dividing the difference in X from a known $X_{EOL}$ by the rate of change $$\Psi \left( RUL = \frac{X - X_{EOL}}{\Psi} \right).$$

2. The method defined in claim 1, wherein said step (E)(ii) includes determining that $\Delta dZ$ has a negative slope greater than about one.

3. The method defined in claim 1, wherein the step of exciting one of said electrodes includes applying an alternating current voltage of note more than about one Volt RMS.

4. The method defined in claim 1, wherein said step of determining the value of RUL if $\Delta dZ$ is negative includes determining if dZ is less than about 25% of $dZ_{MAX}$ and if affirmative providing an indication that RUL is near zero.

* * * * *